United States Patent [19]

Gerhard et al.

[11] Patent Number: 4,516,575
[45] Date of Patent: May 14, 1985

[54] SURGICAL SCALPEL

[75] Inventors: Gregory J. Gerhard, Seattle; William M. Graham, Burton, both of Wash.

[73] Assignee: CooperVision, Inc., Palo Alto, Calif.

[21] Appl. No.: 384,596

[22] Filed: Jun. 3, 1982

[51] Int. Cl.³ ............................................. A61B 17/36
[52] U.S. Cl. .................................. 128/305; 128/744; 33/166; 30/320
[58] Field of Search ................. 128/305, 305.1, 305.5, 128/310, 744, 749, 751, 752, 755, 637; 30/293, 320; 33/18 R, 166

[56] References Cited

U.S. PATENT DOCUMENTS

| | | | |
|---|---|---|---|
| 1,755,535 | 4/1930 | Bratrud | 30/320 |
| 2,704,539 | 3/1955 | Fisher | 128/744 |
| 2,791,034 | 5/1957 | Handy | 33/166 |
| 2,829,439 | 4/1958 | Cunningham | 33/166 |
| 3,608,195 | 9/1971 | Levin | 30/293 X |
| 3,933,148 | 1/1976 | Wyler et al. | 128/744 |
| 3,967,377 | 7/1976 | Wells | 30/320 |
| 4,243,048 | 1/1981 | Griffin | 128/305 X |
| 4,337,576 | 7/1982 | Drost et al. | 30/293 X |

FOREIGN PATENT DOCUMENTS 182855 11/1966 U.S.S.R. .............................. 128/310

OTHER PUBLICATIONS

Albrecht, John G., "A Micrometer Knife", *Trans. American Academy of Opthal. and Otol.*, Mar.-Apr. 1972, pp. 517–518.
Sutor, Anton H. et al., "Bleeding from Standardized Skin Punctures", *Amer. J. Clin. Path.*, 55: 541–550, 1971.

*Primary Examiner*—Edward M. Coven
*Attorney, Agent, or Firm*—Christensen, O'Connor, Johnson & Kindness

[57] ABSTRACT

A surgical scalpel for use in ophthalmic and other forms of surgery having a blade that can be adjustably extended beyond a foot. The scalpel also includes an indicator for showing the length of the blade that is exposed beyond the foot. The indicator can be calibrated to compensate for variations in blade length and other manufacturing tolerances.

6 Claims, 6 Drawing Figures

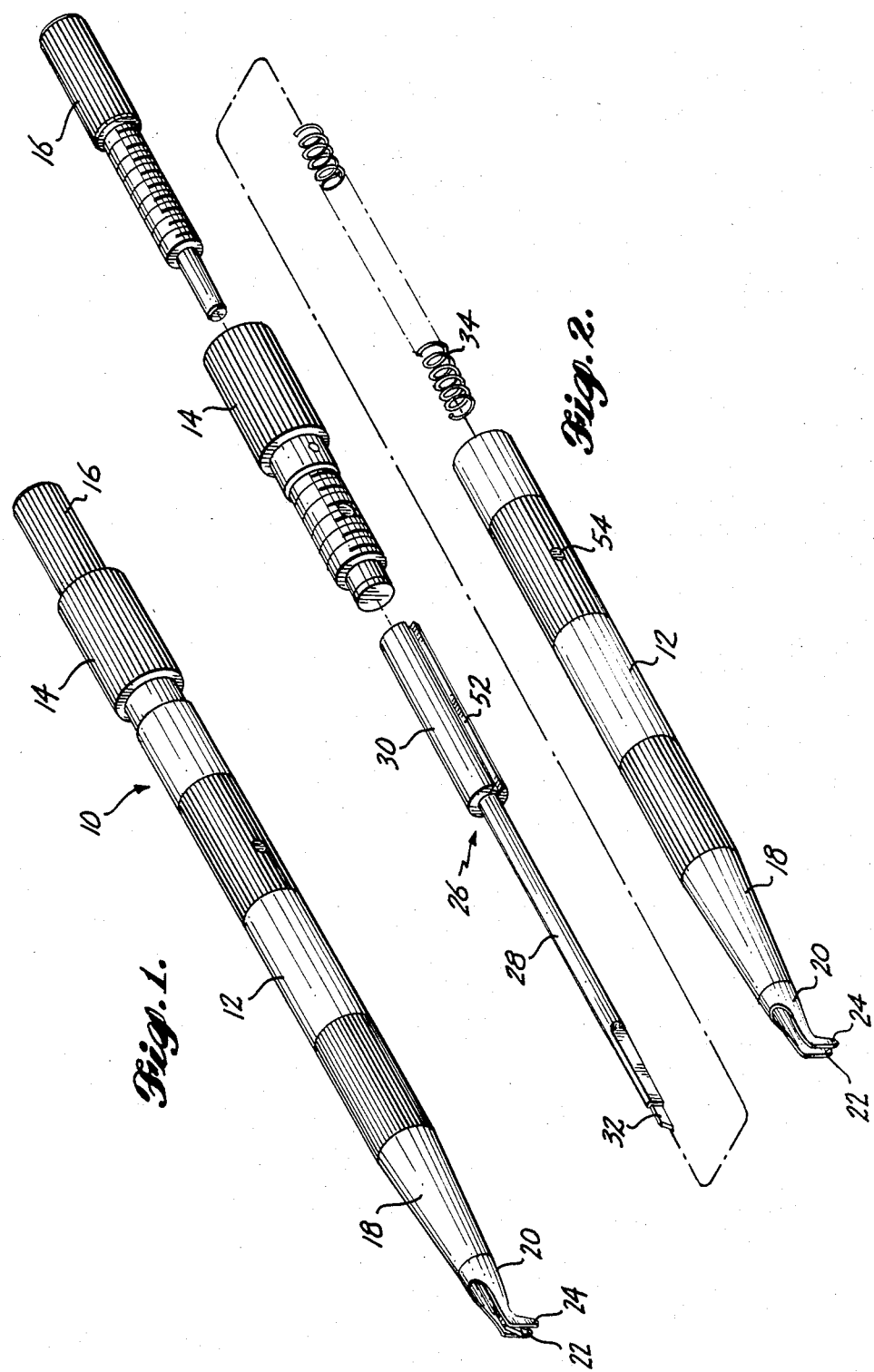

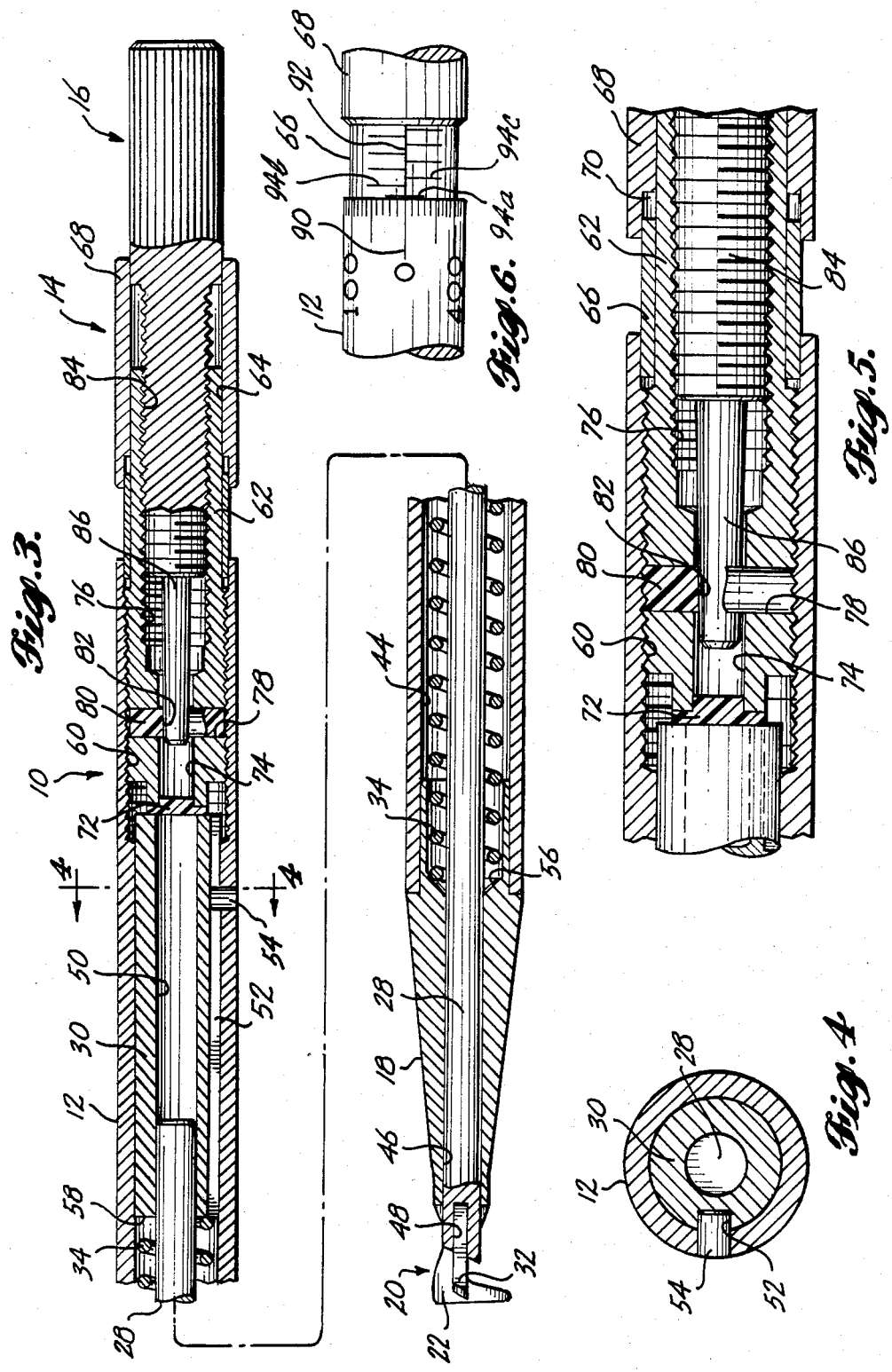

SURGICAL SCALPEL

BACKGROUND OF THE INVENTION

The present invention relates to medical instruments and more particularly to a surgical scalpel having an adjustable depth of cut.

Many surgical procedures including those in the ophthalmic surgery, plastic surgery, and neurosurgery fields require scalpels that have an adjustable depth of cut. Although scalpels are available that provide the surgeon with an adjustable depth of cut, it is desirable in most such scalpels to have ready means for determining the depth of cut provided by the scalpel at any given adjustable setting so that a measurement of the blade protrusion from the instrument is not required upon each readjustment. Moreover, it is desirable that such scalpels be easily calibrated not only upon initial manufacture but upon replacement of a blade or blade holding structure. Moreover, it is desirable for such scalpels to employ a feature that gives infinitely variable adjustment of the blade extension while providing the capability to hold the blade in a desired position without inadvertent or accidental readjustment.

SUMMARY OF THE INVENTION

The foregoing desirable features are provided in a surgical scalpel comprising a barrel or body, a blade holder and blade, an adjustment means for reciprocating the blade holder relative to the barrel, and indicator means to indicate the length of blade exposed. The barrel has a longitudinal channel therethrough. The first end of the barrel terminates in a foot. The corresponding end of the channel opens into the foot. The other end of the channel opens onto the other end of the barrel. The blade holder is mounted for reciprocation in the channel between an extended position wherein the blade is extended beyond the foot and a retracted position wherein the blade is retracted into the channel to provide a protected environment for the blade. The adjustment means is associated with the blade holder and the barrel and includes a means for biasing the blade holder toward the retracted position. The adjustment means also includes a rod that is reciprocably mounted in the channel and coacts with the blade holder to adjustably reciprocate the blade holder between its extended and retracted positions. A means is also provided for releasably affixing the adjustment means to the barrel to prevent the adjustment means from being inadvertently moved.

BRIEF DESCRIPTION OF THE DRAWINGS

A better understanding of the present invention can be derived by reading the ensuing specification in conjunction with the accompanying drawings wherein:

FIG. 1 is an isometric view of the surgical scalpel of the present invention;

FIG. 2 is an exploded isometric view of the surgical scalpel of the present invention;

FIG. 3 is a greatly enlarged longitudinal sectional view of the surgical scalpel of the present invention;

FIG. 4 is a cross-sectional view of the surgical scalpel taken along a section line similar to 4—4 of FIG. 3;

FIG. 5 is a further enlarged longitudinal sectional view of the adjustment member and means for affixing the adjustment member to the barrel in any of a plurality of desirable positions; and FIG. 6 is an enlarged plan view of a segment of the scalpel illustrating the adjustable indicia bearing structure that indicates the amount of blade extension.

DETAILED DESCRIPTION OF THE INVENTION

Referring now to FIGS. 1 and 2, the surgical scalpel 10 of the present invention is configured in the shape of a pencil or other small hand tool and is similarly sized. The scalpel 10 includes a body or barrel 12, an adjustment screw 14 and a lockscrew 16. The barrel 12 has a central longitudinal channel (shown best in FIG. 3) that extends the entire length of the barrel 12. The bottom end of the barrel 12 terminates in a tapered nose 18. The nose 18 tapers radially inwardly from the central portion of the barrel and terminates in foot 20. In this embodiment, the barrel 12 and nose 18 are separately formed; however, the barrel and nose can be formed as a unitary structure if desired. The foot 20 is integrally formed as part of the bottom end of the nose 18. The foot 20 comprises a pair of spaced abutment members 22 and 24 that are spaced on opposite sides of the axis of the barrel. The bottoms or edges of the spaced members 22 and 24 are parallel with each other and lie in a plane that is preferably oriented orthongonally to the axis of the barrel. The foot 20 thus resembles the member given the corresponding name in a sewing machine. The longitudinal channel opens onto the bottom of the barrel between the two abutment members. The foot functions to bear against tissue adjacent an incision, thus limiting the depth of the incision to the length of blade exposed beyond the bottom of the foot.

A blade holder, generally designated 26, comprises a blade shaft 28 and guide 30. The lower end of the blade shaft carries a longitudinally oriented recess into which is inserted a blade 32 of any suitable material, but preferably diamond. The blade holder 26 is reciprocably mounted in the barrel channel along with the spring 34. The adjustment screw 14 threadably engages the interior of the barrel channel and when rotated reciprocates the blade holder 26 against the bias of spring 34. As will be seen in more detail later the lockscrew 16 threads into an axial channel or bore in the adjustment screw and provides a means for locking the adjustment screw to the barrel 12 to secure the blade holder and thus the blade 32 in any desired position.

Referring now to FIGS. 2 and 3 conjunctively, the longitudinal channel 44 extends through the entire length of the barrel 12, opening onto the foot 20 at the bottom of the barrel and also opening onto the upper end of the barrel. The portion 46 of the channel extending through the nose 18 has a slightly smaller diameter than the remainder of channel 44. The blade shaft 28 has a diameter slightly smaller than the diameter of the channel 46 and is reciprocally mounted therein. The bottom end of the blade shaft 28 carries a longitudinally extending recess 48 into which the blade 32 is adhesively or otherwise suitably secured. The upper end of the shaft 28 is inserted into a bore 50 running axially down a guide 30, which has a cylindrical configuration that is slightly smaller in diameter than the diameter of the channel 44 in the barrel 12. The shaft 28 and bore 50 are sized such that the shaft fits in an interference relationship with the bore 50 and thus is secured to the guide 30.

Referring to FIGS. 2, 3 and 4, the guide 30 carries a longitudinally extending groove 52 along the entire length of its outer surface. A radially extending pin 54 is mounted in the barrel and extends into the channel 44 and into the slot 52. The slot 52 and the pin 54 thus coact to prevent the guide 30 from rotating in the channel 44. In this manner, the blade 32, which is rotationally oriented in a predetermined manner relative to the slot 52, is always oriented in the same direction relative to the foot 20 regardless of its longitudinal position within the foot 20. Preferably the blade is oriented such that the cutting edge of the blade when viewed from the bottom of the foot 20 is oriented to run in the same general direction as the bottom edges of the abutment members forming the foot 20.

Referring back to FIGS. 2 and 3, the spring 34 is positioned in the channel 44 between the shoulder 56 formed at the intersection of the barrel channel 44 and the nose channel 46 and the shoulder 58 formed between the lower end of the guide 30 and the blade shaft 28. The spring is under a compression load so that the blade holder and thus the blade 32 is always biased toward a retracted position, that is, a position wherein the blade tip is positioned upwardly from the bottom edges of the foot 20.

The adjustment screw 14 is a generally cylindrical shaped rod having three portions: a lower threaded portion carrying external threads 60 that engage internal threads in the channel 44 in the barrel 12; a central cylindrical portion 62; and an upper end portion 64. The central cylindrical portion 62 has a slightly smaller diameter than the threaded portion 60 and carries a cylindrical sleeve 66 that is mounted snugly on the cylindrical portion 62. The sleeve 66 can be moved both in the circumferential direction and in the axial direction relative to the adjustment screw 14. The fit is sufficiently snug so that the sleeve cannot be moved with the application of only a minor force, but so that upon being manipulated with a predetermined amount of force the sleeve can be repositioned on the central cylindrical portion 62. The upper end of the adjustment screw 64 carries a knurled knob 68 that is fitted over the upper end 64 of the adjustment screw in an interference relationship so that the knob can be grasped and the entire adjustment screw rotated as desired. The bottom end of the knurled knob 68 carries an annular recess 70 having a thickness slightly greater than the sleeve 66. The upper end of the sleeve 66 extends into the recess 70 while the lower end of the sleeve extends under the upper edge or top of the barrel 12 and into the upper end of channel 44. The purpose of the sleeve will be discussed in more detail below in conjunction with FIGS. 3 and 6. The primary function of the adjustment screw 14 is to selectively position the blade holder 26 in the barrel channel 44. The threaded portion of the screw 14 engages matching internal threads in the upper end of the channel 44. The lower end of the adjustment screw includes friction reducing cap 72 positioned such that it is interposed between the lower end of the screw and guide 30.

Referring conjunctively to FIGS. 2, 3 and 5, the adjustment screw 14 carries an axial bore 74 at its lower end having a first diameter. This bore transitions into a second bore 76 of larger diameter that carriers internal threads. A diametrically oriented bore 78 extends through the threaded portion 60 of the adjustment screw and intersects the smaller diameter bore 74. This diametrically oriented bore 78 carries a resilient and expandable plug 80, composed of any suitable polymeric material such as an acetal resin. The plug 80 is inserted into the bore 78 before the external threads on the bottom threaded portion 60 of the plug are formed. Thus the resilient, expandable plug 80 also carries threads in its outer ends that provide continuity to the external threads on the lower portion 60 of the adjustment screw. Another axial bore 82 oriented coaxially with the smaller diameter bore 74 is formed through the central portion of the plug 80. The axial bore 82 in the plug has a diameter that is slightly less than the smaller diameter bore 74 in the adjustment screw. Another threaded member 84 has external threads that engage the internal threads in the larger diameter bore 76. The bottom end of the threaded member 84 carries a tapered pin 86. The larger end of the tapered pin 86 lies adjacent the threaded member 86 while the smaller end extends through and beyond the bore 82 and the plug 80. As the threaded member 84 is threaded down into the adjustment screw 14, the sides of the tapered pin 86 bear radially outwardly with increasing force against the surfaces of the bore 82. As force is exerted on the expandable plug 80, the pin is expanded outwardly against the threaded sidewalls of the upper portion of the channel 44 in the barrel 12. When sufficient force is exerted on the plug 80, resistance to rotation of the adjustment screw 14 is created by the friction of the outer ends of the plug 80 on the threaded surface of the channel wall. In this manner, the coaction of the threaded member 84, tapered pin 86 and resilient plug 80 on the inner walls of the barrel serve to selectively fix the adjustment screw in any desired position, thereby preventing its inadvertent or accidental movement once the blade extension beyond the foot 20 has been set to a desired degree.

Referring now to FIGS. 3 and 6, the surgical scalpel has a plurality of indicia associated with the barrel and adjustment screw for providing a readout on the amount of blade extension. The exterior surface of the upper end of the barrel 12 carries a plurality of circumferentially spaced gradation lines 90. These gradations extend longitudinally along the outer surface of the barrel 12 and divide the outer surface into a predetermined number of circumferential increments. The basic division is 5 segments with subdivisions of the segments being multiples thereof. One of the basic subdivision demarking lines 90 is labeled zero and the other lines are labeled 100, 200, 300 and 400 respectively. A complementary, longitudinally extending line 92 is placed on the sleeve 66, which is mounted on the central cylindrical portion 62 of the adjustment screw 14. Additionally, circumferentially extending, longitudinally spaced gradation lines 94a, 94b, 94c . . . divide the longitudinally extending line 92 into a plurality of equal increments. The bottom circumferentially extending line 94a intersects and extends on both sides of the line 92 while other lines 94 extend alternately from opposite sides of the line 92. The line 94a is a zero line. The threads on the adjustment screw 14 are thus sized so that one revolution of the adjustment screw will preferably advance the adjustment screw and thus the blade holder and blade, for example 0.5 mm. The distance between the gradation lines 94a to 94b is therefore preferably set at 0.5 mm. Similarly, the distance between the gradations 94b to 94c and so on is set at 0.5 mm.

To calibrate the reading of blade extension, the adjustment screw 14 is rotated so that the very tip of the knife blade coincides with the plane formed by the bottom edges of the foot 20. When the blade is so positioned, the sleeve 66 is moved axially relative to the adjustment screw such that the bottom zero line 94a coincides with the location of the upper lip or edge of the barrel 12. Similarly, the zero line 92 on the sleeve is positioned so it corresponds to and aligns with the zero line 90 formed on the outer surface of the barrel 12. When so calibrated, the amount of extension of the blade beyond the plane of the foot 20 can be determined by merely reading first the indicia on the cylindrical sleeve 66 to determine the major increment that whether the blade has been extended some fraction of 0.5, 1.0 or 1.5 millimeters and thereafter reading the fraction of the extension by reading the particular increment on the outer portion of the barrel 12 with respect to the location of the zero line 92 on the sleeve 66. For example, if the line 92 is positioned adjacent the line marked 400 and the upper lip of the barrel 12 lies between the lines 94b and 94c on the sleeve 66, the blade is extended 0.9 mm, provided the device has been properly calibrated.

The present invention has been described in relation to a preferred embodiment. One of ordinary skill after reviewing the foregoing specification will be able to make various changes, substitutions of equivalents and other alterations to the invention as described without departing from the broad concepts disclosed herein. For example, a variety of incision depth limiting structures or alternatives therefore can be substituted for the foot 20 without changing the basic nature of the disclosed invention. Further, the scalpel has been disclosed in relation to a preferred embodiment for use in ophthalmic surgery. It is to be understood, however, that the scalpel can be utilized in many forms of surgery in which incisions to precise depths must be performed. Examples of such surgery include plastic surgery as well as neurosurgery. It is therefore intended that the Letters Patent granted hereon be limited only by the definition contained in the appended claims and equivalents thereof.

The embodiments of the invention in which an exclusive property or privilege is claimed are defined as follows:

1. A surgical scalpel comprising:
    a barrel having a longitudinal channel therethrough, the channel having first and second ends corresponding to first and second ends of the barrel;
    a blade holder having a blade affixed to one end thereof, the blade holder being mounted for reciprocation in the channel between an extended position wherein the blade extends beyond the first end of the barrel and a retracted position;
    adjustment means reciprocably mounted in the channel and coacting with the blade holder to adjustably reciprocate the blade holder between the extended and retracted positions, the adjustment means comprising a rod having intersecting axial and transverse bores extending therethrough, an expandable plug positioned in the transverse bore and having a bore therethrough that is oriented substantially coaxially with the axial bore in the rod, and means for moving the plug outwardly to engage the walls of the channel, the means for moving the plug comprising a tapered pin reciprocably mounted in the axial bore in the rod and the bore in the plug.

2. The scalpel of claim 1, wherein the tapered pin has a head with external threads thereon, the axial bore having internal threads therein, the head threadably engaging the axial bore for reciprocating adjustment of the pin in the axial bore and the bore in the plug.

3. A surgical scalpel comprising:
    a barrel having a longitudinal channel therethrough, the channel having first and second ends corresponding to first and second ends of the barrel;
    a blade holder having a blade affixed to one end thereof, the blade holder being mounted for reciprocation in the channel between an extended position wherein the blade extends beyond the first end of the barrel and a retracted position;
    means for preventing rotational movement of the blade holder in the channel;
    adjustment means comprising a rod, a portion of the rod being threadably mounted in the channel such that rotation of the rod is operative to adjustably reciprocate the blade holder between the extended and retracted positions;
    means for selectively affixing the rod to the barrel; and,
    means for resiliently biasing the blade holder into contact with the rod.

4. The scalpel of claim 3, further comprising a friction-reducing cap interposed between the blade holder and the rod.

5. A surgical scalpel, comprising:
    a barrel having a longitudinal channel therethrough, the channel having first and second ends corresponding to first and second ends of the barrel;
    a blade holder having a blade affixed to one end thereof, the blade holder being mounted for reciprocation in the channel between an extended position wherein the blade extends beyond the first end of the barrel and a retracted position;
    adjustment means comprising a rod having a transverse bore, a portion of the rod being threadably mounted in the channel such that rotation of the rod is operative to adjustably reciprocate the blade holder between the extended and retracted positions, the adjustment means including a plug of expandable material positioned in the transverse bore; and,
    means for causing the plug to move outward into contact with the barrel to prevent the adjustment means from being inadvertently moved.

6. The scalpel of claim 5, wherein the rod includes external threads and wherein the outer surface of the plug includes threads that are continuous with the external threads of the rod.

* * * * *